(12) United States Patent
Ueda

(10) Patent No.: US 11,033,691 B2
(45) Date of Patent: Jun. 15, 2021

(54) MEDICAL PUNCTURE NEEDLE

(71) Applicant: TERUMO KABUSHIKI KAISHA, Tokyo (JP)

(72) Inventor: Takehiko Ueda, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 216 days.

(21) Appl. No.: 16/143,216

(22) Filed: Sep. 26, 2018

(65) Prior Publication Data

US 2019/0091415 A1 Mar. 28, 2019

(30) Foreign Application Priority Data

Sep. 27, 2017 (JP) .............................. JP2017-187158
Jul. 19, 2018 (JP) .............................. JP2018-136040

(51) Int. Cl.
*A61M 5/32* (2006.01)
*A61M 25/00* (2006.01)

(52) U.S. Cl.
CPC ...... *A61M 5/3286* (2013.01); *A61M 25/0084* (2013.01); *A61M 2025/0089* (2013.01)

(58) Field of Classification Search
CPC .... A61M 5/32; A61M 5/3286; A61M 5/3295; A61M 5/3297; A61M 5/3298; A61M 25/065; A61M 25/0084; A61M 2025/0085–0093; A61M 2025/0656; A61B 5/150381; A61B 5/150389; A61B 5/150396; A61B 5/150412; A61B 5/150419; A61B 5/150427; A61B 5/150442; A61B 5/15045; A61B 5/150458

See application file for complete search history.

(56) References Cited

U.S. PATENT DOCUMENTS

| | | | | |
|---|---|---|---|---|
| 3,308,822 A | * | 3/1967 | De Luca | A61M 5/3286 604/274 |
| 5,752,942 A | * | 5/1998 | Doyle | B24B 19/16 604/274 |
| 7,070,583 B1 | * | 7/2006 | Higuchi | A61M 5/3286 604/164.06 |

FOREIGN PATENT DOCUMENTS

JP 2014-004249 A 1/2014

* cited by examiner

*Primary Examiner* — Kami A Bosworth
(74) *Attorney, Agent, or Firm* — Foley & Lardner LLP

(57) ABSTRACT

A medical puncture needle comprising includes: a rod-shaped body portion; and a blade surface formed at a distal end portion of the rod-shaped body portion. The blade surface includes: a first blade surface portion that is inclined with respect to a central axis of the body portion and extends to a tip, and a second blade surface portion that is formed on a back side of the first blade surface portion. A blade edge extending to the tip is formed by a ridgeline at which the first blade surface portion intersects the second blade surface portion. The second blade surface portion comprises a first plane and a second plane having different angles with respect to a virtual plane including the central axis passing through the tip at an orthogonal cross-section that is orthogonal to the central axis.

16 Claims, 9 Drawing Sheets

I - I CROSS-SECTION

II - II CROSS-SECTION

III-III CROSS-SECTION

IV-IV CROSS-SECTION

V-V CROSS-SECTION

VI-VI CROSS-SECTION

MEDICAL PUNCTURE NEEDLE

CROSS-REFERENCE TO RELATED APPLICATION

This patent application claims priority to Japanese Application No. 2017-187158, filed on Sep. 27, 2017. The contents of this application are hereby incorporated by reference in their entirety.

BACKGROUND

The present disclosure relates to a medical puncture needle.

Conventionally, there is a known medical puncture needle, such as a blood sampling needle and an indwelling needle for infusion, that includes, at a distal end portion, a blade surface inclined with respect to the longitudinal direction of the puncture needle in order to alleviate pain when puncturing a human body with the puncture needle.

JP 2014-004249 A discloses a puncture needle of this type having a blade surface whose blade surface shape is called a "back-cut bevel point" (hereinafter referred to simply as a "back-cut type"). The puncture needle having the back-cut type blade surface disclosed in JP 2014-004249 A is superior in rectilinearity, and thus, is used to puncture a target site at a relatively deep position in the body from a body surface such as puncture into an artery and puncture into a central vein.

SUMMARY

The puncture needle having a back-cut type blade surface disclosed in JP 2014-004249 A includes a flat-cut surface as a blade surface portion on the front side and a planar back-cut surface as a blade surface portion on the back side, and forms a linear cutting edge as a blade edge extending to a tip using a ridgeline where the flat-cut surface and the back-cut surface intersect with each other. Thus, when inserting the puncture needle disclosed in JP 2014-004249 A, this blade edge functions to incise the skin so that it is possible to reduce penetration resistance, and thus, the pain sensed by a patient or the like is alleviated.

However, when the thickness of the puncture needle becomes thin, for example, the planar back-cut surface becomes small so that it is difficult to secure a length of the cutting edge to incise the skin. Thus, the skin can be incised by the cutting edge as the blade edge in the vicinity of the tip, but an outer surface of the puncture needle is inserted to forcibly push an incision apart when a proximal end of the cutting edge on the side opposite to the tip passes through the skin, and thus, the patient feels pain when the incision of the skin is pushed apart.

An object of certain embodiments described herein is to provide a medical puncture needle having a configuration of a back-cut type blade surface capable of easily securing a length of a blade edge.

According to a first aspect, a medical puncture needle includes a blade surface formed at a distal end portion of a rod-shaped body portion. The blade surface includes a first blade surface portion that is inclined with respect to a central axis of the body portion and extends to a tip; and a second blade surface portion that is formed on a back side of the first blade surface portion and forms a blade edge extending to the tip by a ridgeline intersecting with the first blade surface portion. The second blade surface portion includes a first plane and a second plane having different angles with respect to a virtual plane including the central axis passing through the tip at an orthogonal cross-section orthogonal to the central axis. The second plane is at a position farther from the tip than the first plane in a distal end view of the blade surface as viewed from a side of the tip along a central axis direction parallel to the central axis, and the angle of the second plane with respect to the virtual plane in the orthogonal cross-section is smaller than the angle of the first plane with respect to the virtual plane in the orthogonal cross-section.

According to one embodiment, the blade edge includes a blade edge portion formed by a ridgeline where the first blade surface portion and the first plane of the second blade surface portion intersect with each other, and the blade edge portion extends to the tip.

According to one embodiment, when the blade edge portion is a first blade edge portion, the blade edge includes a second blade edge portion formed by a ridgeline where the first blade surface portion and the second plane of the second blade surface portion intersect with each other, and the second blade edge portion is continuous with an outer circumferential surface of the body portion in the distal end view.

According to one embodiment, a length of the first blade edge portion is longer than a length of the second blade edge portion in the distal end view.

According to one embodiment, the second blade surface portion includes at least one third plane, which has a different angle with respect to the virtual plane in the orthogonal cross-section from the first plane and the second plane and is positioned between the first plane and the second plane in the distal end view. The angle of the third plane with respect to the virtual plane in the orthogonal cross-section is smaller than the angle of the first plane with respect to the virtual plane in the orthogonal cross-section, and is larger than the angle of the second plane with respect to the virtual plane in the orthogonal cross-section.

According to one embodiment, the blade edge includes at least one third blade edge portion, formed by a ridgeline where the first blade surface portion and the third plane of the second blade surface portion intersect with each other, at a position between the first blade edge portion and the second blade edge portion in the distal end view. Each of the first blade edge portion, the second blade edge portion, and the at least one third blade edge portion has a smaller angle with respect to the virtual plane at a position farther from the tip in the distal end view.

According to one embodiment, a length of the first blade edge portion is longer than a total length obtained by adding a length of the at least one third blade edge portion, in the distal end view According to one embodiment, a ridge portion formed by a ridgeline where the second plane and the third plane intersect with each other extends along the central axis.

According to one embodiment, a ridge portion formed by a ridgeline where the first plane and the third plane intersect with each other extends along the central axis.

According to one embodiment, when the blade edge is the first blade edge, the blade surface includes a third blade surface portion that is formed on a back side of the first blade surface portion and forms a second blade edge extending to the tip by a ridgeline intersecting with the first blade surface portion, and the second blade surface portion and the third blade surface portion form a third blade edge extending to the tip along the central axis by a ridgeline where the second blade surface portion and the third blade surface portion intersect with each other.

According to one embodiment, the third blade surface portion has a shape symmetric with the second blade surface portion with respect to the virtual plane.

According to a second aspect, a medical puncture needle includes a blade surface formed at a distal end portion of a rod-shaped body portion. The blade surface includes a first blade surface portion that is inclined with respect to a central axis of the body portion and extends to a tip; and a second blade surface portion that is formed on a back side of the first blade surface portion and forms a blade edge extending to the tip by a ridgeline intersecting with the first blade surface portion. The second blade surface portion includes a plurality of planes having different angles with respect to a virtual plane including the central axis passing through the tip at an orthogonal cross-section orthogonal to the central axis. The blade edge extends so as to protrude to a radially outer side of the body portion from a straight line connecting both ends of the blade edge in a distal end view of the blade surface as viewed from a side of the tip along a central axis direction parallel to the central axis.

According to a third aspect, a medical puncture needle includes a blade surface formed at a distal end portion of a rod-shaped body portion. The blade surface includes a first blade surface portion that is inclined with respect to a central axis of the body portion and extends to a tip; and a second blade surface portion that is formed on a back side of the first blade surface portion and forms a blade edge extending to the tip by a ridgeline intersecting with the first blade surface portion. The second blade surface portion includes a plurality of planes having different angles with respect to a virtual plane including the central axis passing through the tip at an orthogonal cross-section orthogonal to the central axis. The blade edge includes a first blade edge portion that extends to the tip and is formed by a ridgeline where the first blade surface portion and a first plane that is one of the plurality of planes intersect with each other. The first blade edge portion extends from the tip to a terminal point positioned on a radially outer side of the body portion from a straight line connecting both ends of the blade edge in a distal end view of the blade surface as viewed from a side of the tip along a central axis direction parallel to the central axis.

According to a fourth aspect, a medical puncture needle includes a blade surface formed at a distal end portion of a rod-shaped body portion. The blade surface includes a first blade surface portion that is inclined with respect to a central axis of the body portion and extends to a tip; and a second blade surface portion that is formed on a back side of the first blade surface portion and forms a blade edge extending to the tip by a ridgeline intersecting with the first blade surface portion. The second blade surface portion includes a first plane, a second plane, and at least one third plane that have different angles with respect to a virtual plane passing through the tip and including the central axis in an orthogonal cross-section orthogonal to the central axis. The second plane is at a position farther from the tip than the first plane in a distal end view of the blade surface as viewed from a side of the tip along a central axis direction parallel to the central axis, and the at least one third plane is positioned between the first plane and the second plane in the distal end view. The blade edge includes: a first blade edge portion that extends to the tip and is formed by a ridgeline where the first blade surface portion and the first plane of the second blade surface portion intersect with each other; a second blade edge portion that is continuous to an outer circumferential surface of the body portion in the distal end view and is formed by a ridgeline where the first blade surface portion and the second plane of the second blade surface portion intersect with each other; and at least one third blade edge portion that is formed by a ridgeline where the first blade surface portion and the third plane of the second blade surface portion intersect with each other at a position between the first blade edge portion and the second blade edge portion in the distal end view. In the distal end view, a length of the first blade edge portion is longer than a total length obtained by adding a length of the at least one third blade edge portion.

According to certain embodiments of the present disclosure, it is possible to provide a medical puncture needle having the configuration of the back-cut type blade surface in which the length of the blade edge is easily secured.

DETAILED DESCRIPTION

Figure 1A:
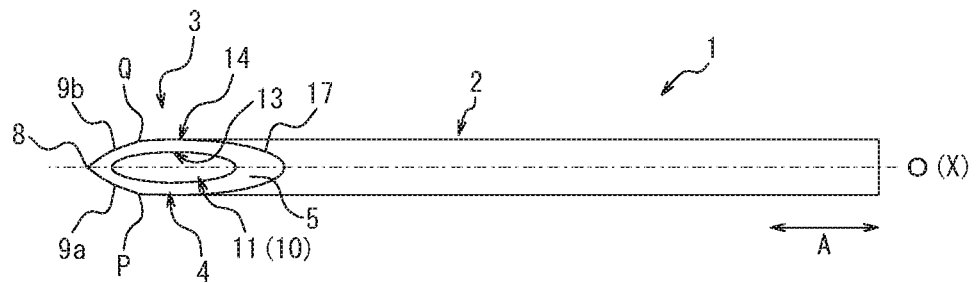
FIG. 1A is a front view of a puncture needle 1.

Hereinafter, embodiments of a medical puncture needle according to the present disclosure will be described with reference to FIGS. 1A to 7. The same reference numerals are used for members and parts common in the respective drawings.

Figure 1B:
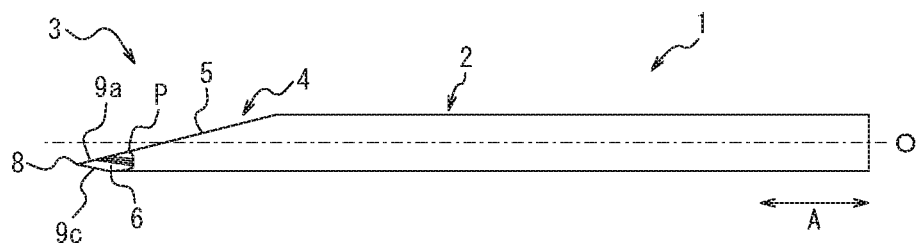
FIG. 1B is a side view of the puncture needle 1.
Figure 1C:
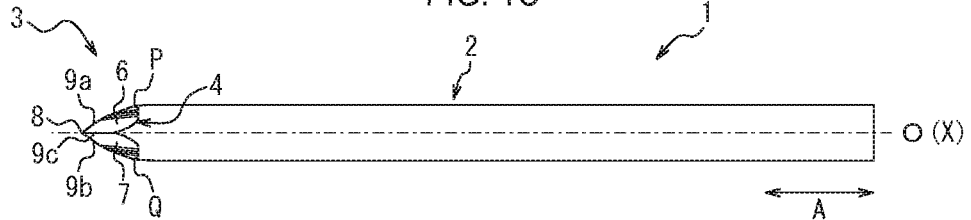
FIG. 1C is a rear view of the puncture needle 1.
Figure 1D:
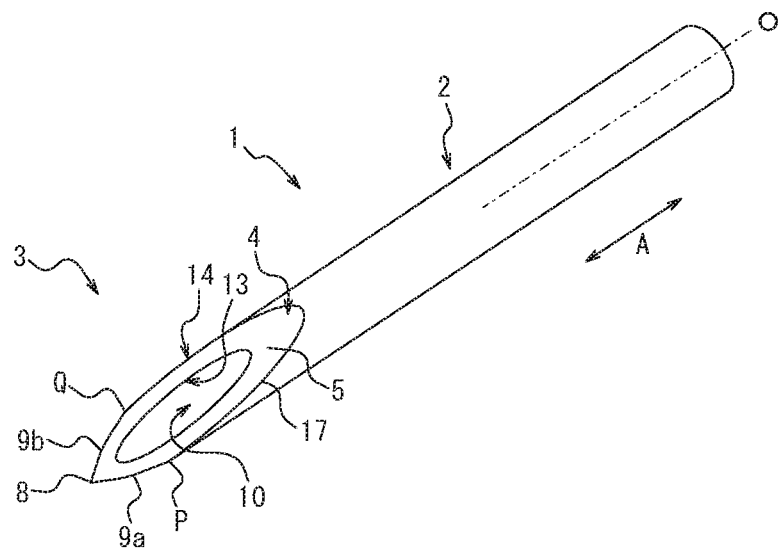
FIG. 1D is a perspective view of the puncture needle 1.

FIGS. 1A to 1D are views illustrating a puncture needle 1 according to one embodiment. Specifically, FIG. 1A is a front view illustrating the front of the puncture needle 1. FIG. 1B is a side view of the puncture needle 1. FIG. 1C is a rear view illustrating the rear on the opposite side of the front of the puncture needle 1. FIG. 1D is a perspective view of the puncture needle 1.

As illustrated in FIGS. 1A to 1D, the puncture needle 1 includes a rod-shaped body portion 2, and a blade surface 4 is formed at a distal end portion 3 of the body portion 2.

Figure 2A:
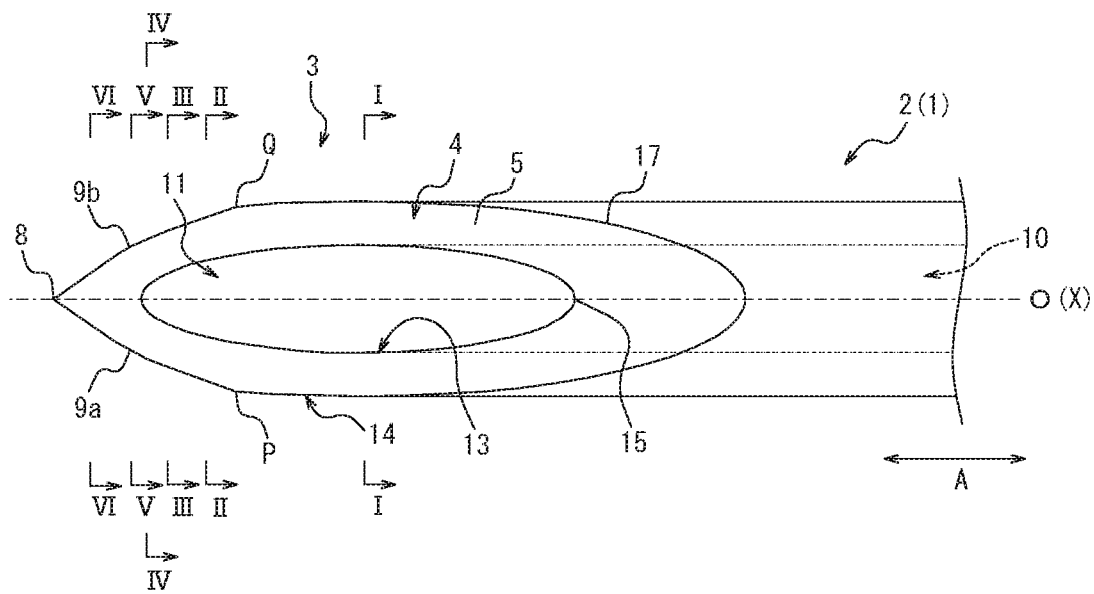
FIG. 2A is an enlarged front view illustrating a part of the front view of the puncture needle 1 illustrated in FIG. 1A in an enlarged manner.
Figure 2B:
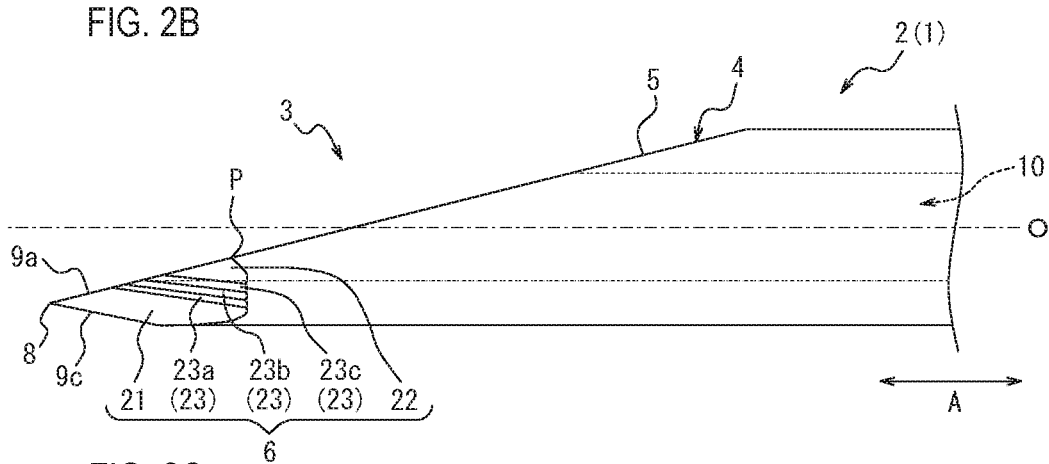
FIG. 2B is an enlarged side view illustrating a part of the side view of the puncture needle 1 illustrated in FIG. 1B in an enlarged manner.
Figure 2C:
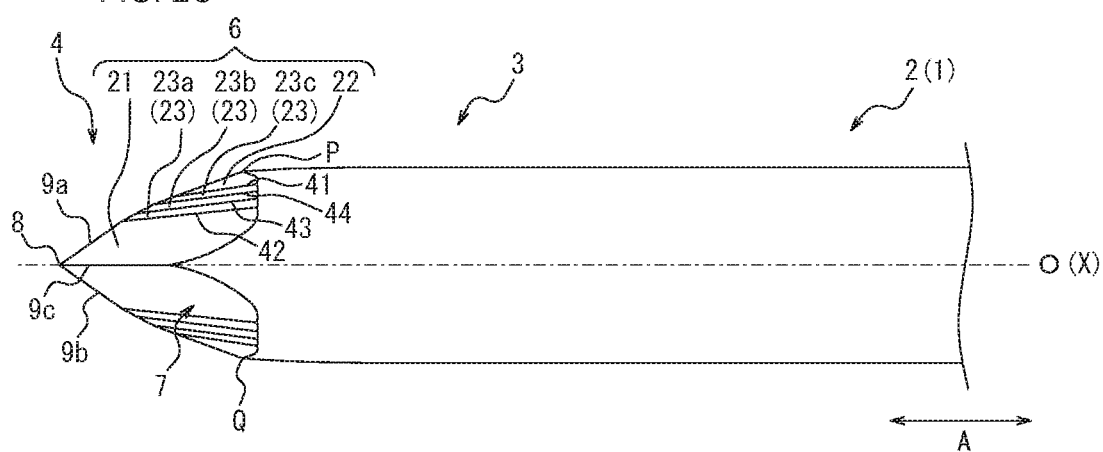
FIG. 2C is an enlarged rear view illustrating a part of the rear view of the puncture needle 1 illustrated in FIG. 1C in an enlarged manner.

FIG. 2A is an enlarged front view illustrating the vicinity of the distal end portion 3 of the body portion 2 of the puncture needle 1 illustrated in FIG. 1A in an enlarged manner. FIG. 2B is an enlarged side view illustrating the vicinity of the distal end portion 3 of the body portion 2 of the puncture needle 1 illustrated in FIG. 1B in an enlarged manner. FIG. 2C is an enlarged rear view illustrating the vicinity of the distal end portion 3 of the body portion 2 of the puncture needle 1 illustrated in FIG. 1C in an enlarged manner.

As illustrated in FIGS. 2A to 2C, the body portion 2 of this embodiment includes a hollow portion 10 communicating from a proximal end portion of the body portion 2 to the distal end portion 3 in a central axis direction A parallel to a central axis O of the body portion 2. Hereinafter, a description will be given by exemplifying the puncture needle 1 including the hollow portion 10, but a solid puncture needle without the hollow portion 10 may be used.

The body portion 2 of this embodiment is a hollow rod-shaped, that is, tubular pipe body. More specifically, the body portion 2 of this embodiment is a pipe body having a substantially circular cross-sectional outline. Here, the "cross-section" and the "cross-sectional outline" refers to a transverse cross-section orthogonal to the central axis O of the body portion 2.

The blade surface 4 is constituted by a plurality of blade surface portions, and the blade surface 4 of this embodiment includes a first blade surface portion 5 as a front-side blade surface portion, and a second blade surface portion 6 and a third blade surface portion 7 as rear-side blade surface portions as illustrated in FIGS. 1A to 2C. That is, the puncture needle 1 includes the back-cut type blade surface 4.

The first blade surface portion 5 is inclined with respect to the central axis O of the body portion 2 and extends to a tip 8. Further, the first blade surface portion 5 of this embodiment is formed of one plane. The first blade surface portion 5 of this embodiment is a plane inclined at a predetermined angle such as 12 degrees and 18 degrees with respect to the central axis O. The "tip" is a distal end of the body portion 2 in the central axis direction A, which means a distal end of the puncture needle 1.

As illustrated in FIGS. 1A to 2C, the second blade surface portion 6 is formed on the back side of the first blade surface portion 5 and forms a first blade edge 9a extending to the tip 8 by a ridgeline intersecting with the first blade surface portion 5. The second blade surface portion 6 includes at least a plurality of planes. More specifically, the second blade surface portion 6 of this embodiment is constituted by the plurality of planes. Details of each plane of the second blade surface portion 6 will be described later.

As illustrated in FIGS. 1A to 2C, the third blade surface portion 7 is formed on the back side of the first blade surface portion 5 and has a second blade edge 9b extending to the tip 8 by a ridgeline intersecting with the first blade surface portion 5. The third blade surface portion 7 includes at least a plurality of planes. More specifically, the third blade surface portion 7 of this embodiment is constituted by the plurality of planes. Details of each plane of the third blade surface portion 7 will be described later.

As illustrated in FIG. 2A, an inner edge 13 of the first blade surface portion 5 includes an opening 11, which is one end of the hollow portion 10 on the tip 8 side. As illustrated in FIG. 2A, an outer edge 14 of the first blade surface portion 5 is formed of the first blade edge 9a and the second blade edge 9b extending to the tip 8, and a proximal-end-side outer edge portion 17.

More specifically, the first blade edge 9a extends from the tip 8 to a terminal point P on the outer edge 14 of the first blade surface portion 5. Further, the second blade edge 9b extends from the tip 8 to a terminal point Q on the outer edge 14 of the first blade surface portion 5. Therefore, the proximal-end-side outer edge portion 17 of the outer edge 14 of the first blade surface portion 5 described above is a portion closer to the proximal end in the central axis direction A than the terminal points P and Q.

In this embodiment, the second blade surface portion 6 and the third blade surface portion 7 form a third blade edge 9c extending to the tip 8 along the central axis O by a ridgeline where the second blade surface portion 6 and the third blade surface portion 7 intersect with each other.

As described above, the first blade edge 9a, the second blade edge 9b, and the third blade edge 9c are formed on the blade surface 4 of the puncture needle 1 of this embodiment. Thus, when the puncture needle 1 is inserted from a surface of a body into the body, the first blade edge 9a, the second blade edge 9b, and the third blade edge 9c serve to incise the skin so that it is possible to reduce penetration resistance.

In this embodiment, the second blade surface portion 6 and the third blade surface portion 7 have a shape symmetric with respect to a virtual plane passing through the tip 8 and including the central axis O. In this embodiment, the third blade edge 9c formed by the ridgeline where the second blade surface portion 6 and the third blade surface portion 7 intersect with each other is a straight line substantially parallel to the central axis direction A, and the third blade edge 9c also extends on the virtual plane. In this embodiment, the above-described virtual plane is orthogonal to the first blade surface portion 5. Hereinafter, the above-described virtual plane passing through the tip 8 and including the central axis O will be simply referred to as a "center plane X" for convenience of description. The puncture needle 1 of this embodiment is a hollow needle having a symmetric configuration with respect to the center plane X.

Next, a shape of the blade surface 4 in a cross-section that is orthogonal to the central axis O of the body portion 2 will be described with reference to FIGS. 3A to 3F. Hereinafter, the cross-section orthogonal to the central axis O of the body portion 2 will be simply referred to as the "orthogonal cross-section" for convenience of description. FIGS. 3A to 3F are views illustrating orthogonal cross-sections at different positions in the central axis direction A, respectively.

Figure 3A:
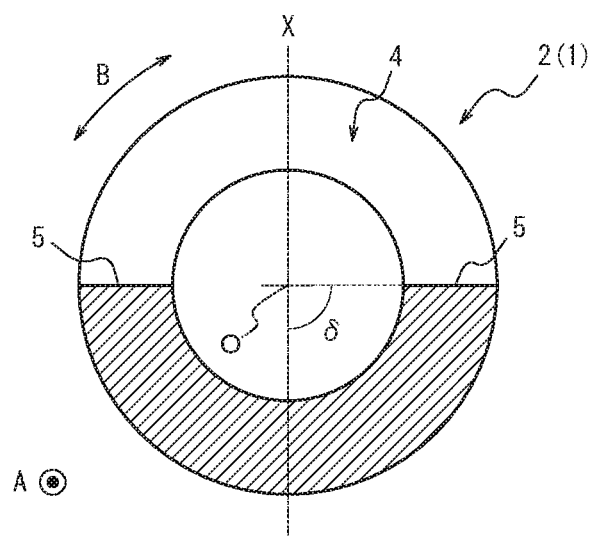
FIG. 3A is a cross-sectional view taken along line I-I of FIG. 2A.

Specifically, FIG. 3A is the orthogonal cross-section in a region where only the first blade surface portion 5 of the blade surface 4 is formed in the central axis direction A. FIGS. 3B to 3F illustrate the orthogonal cross-sections in a region where the first blade surface portion 5, the second blade surface portion 6, and the third blade surface portion 7 of the blade surface 4 are formed in the central axis direction A.

As illustrated in FIG. 3A to FIG. 3F, the first blade surface portion 5 is formed by a plane that extends to be substantially orthogonal with respect to the center plane X in the orthogonal cross-section regardless of the position in the central axis direction A. In other words, an angle δ of the first blade surface portion 5 with respect to the center plane X in the orthogonal cross-section is approximately 90 degrees regardless of the position in the central axis direction A.

Figure 3B:
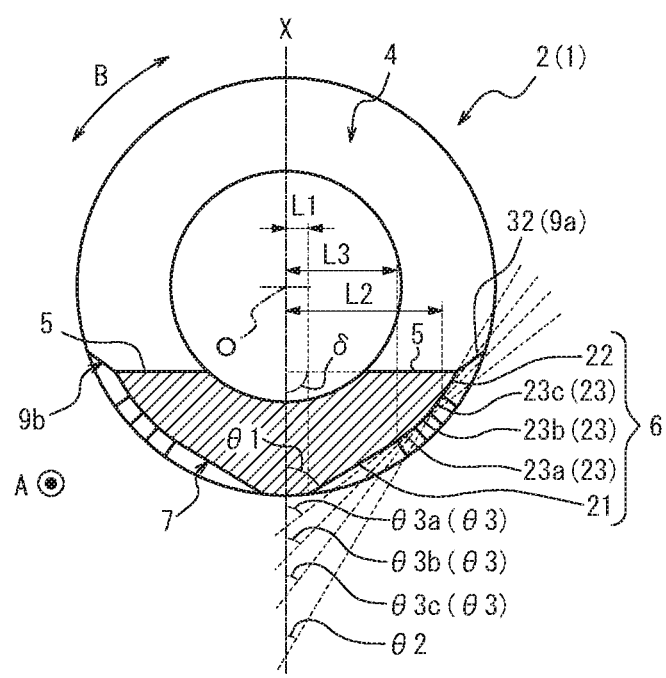
FIG. 3B is a cross-sectional view taken along line II-II in FIG. 2A.
Figure 3C:
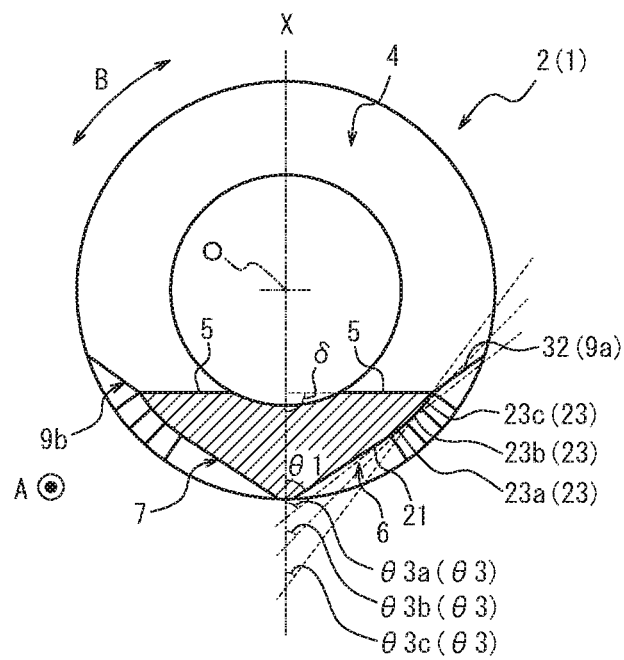
FIG. 3C is a cross-sectional view taken along line III-III in FIG. 2A.
Figure 3D:
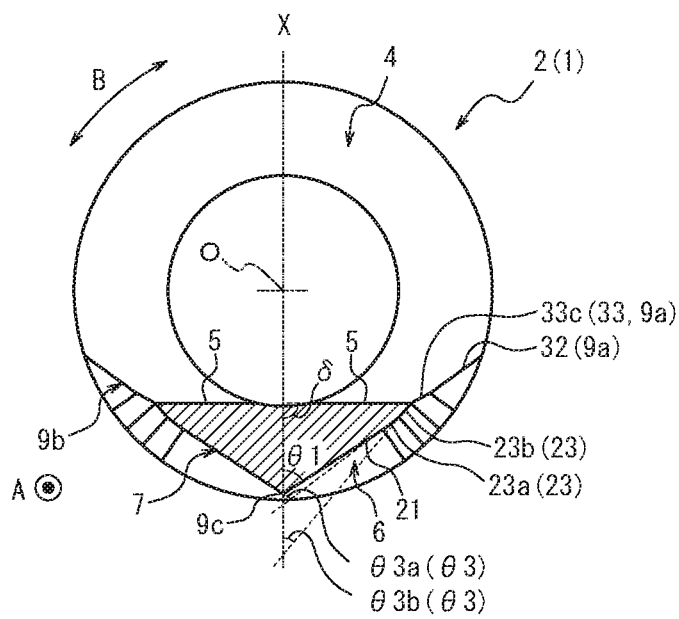
FIG. 3D is a cross-sectional view taken along line IV-IV in FIG. 2A.
Figure 3E:
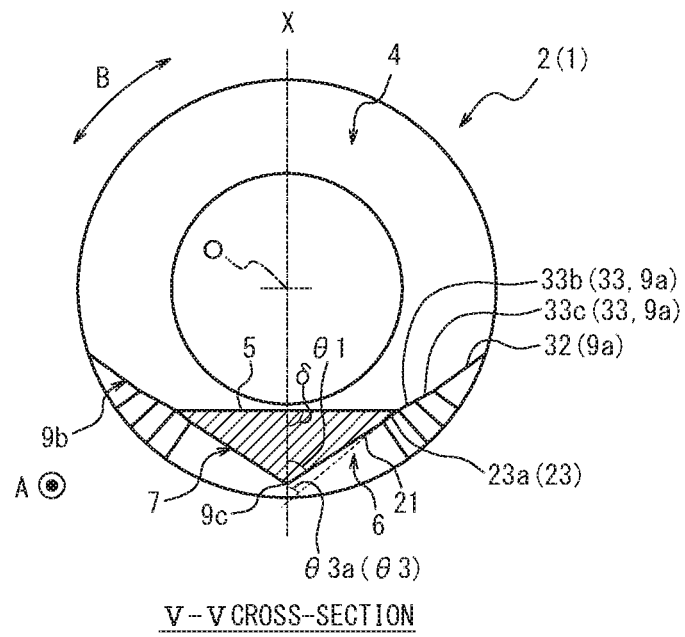
FIG. 3E is a cross-sectional view taken along line V-V in FIG. 2A.
Figure 3F:
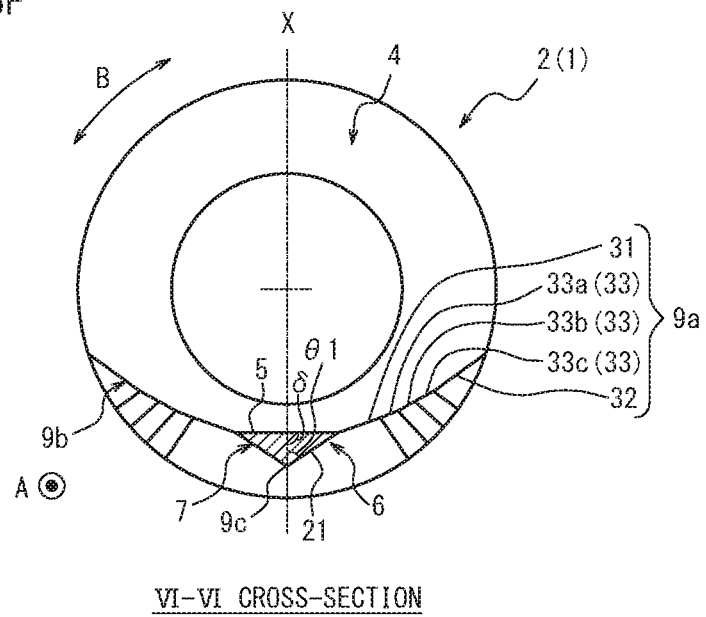
FIG. 3F is a cross-sectional view taken along line VI-VI in FIG. 2A.

As illustrated in FIGS. 3B to 3F, the second blade surface portion 6 includes a first plane 21, a second plane 22, and a plurality of third planes 23 having different acute angles θ with respect to the center plane X in the orthogonal cross-section. Further, the first plane 21, the second plane 22, and the plurality of third planes 23 are formed at positions at different distances from the center plane X as illustrated in FIGS. 3B to 3F. The distance from the center plane X is farther in the order of the first plane 21, the plurality of third planes 23, and the second plane 22. The "distance from the center plane X" referred herein means the shortest distance from the center plane X in a direction orthogonal to the center plane X in the orthogonal cross-section. FIG. 3B illustrate a distance L1 of the first plane 21 from the center plane X, a distance L2 of the second plane 22 from the center plane X, and a distance L3 of one third plane 23 from the center plane X.

As illustrated in FIG. 3B, an angle θ2 of the second plane 22 is smaller than an angle θ1 of the first plane 21. Further, an angle θ3 of the third plane 23, which is an arbitrary one of the plurality of third planes 23, is smaller than the angle θ1 of the first plane 21 and is larger than the angle θ2 of the second plane 22 as illustrated in FIG. 3B.

In particular, three third planes 23a, 23b, and 23c are provided as the plurality of third planes 23 in this embodiment. The third plane 23a is provided at a position closest to the tip 8 in a circumferential direction B of the body portion 2 among the three third planes 23a, 23b, and 23c. The third plane 23c is provided at a position farthest from the tip 8 in the circumferential direction B among the three third planes 23a, 23b and 23c. The third plane 23b is provided at a position between the other two third planes 23a and 23b in the circumferential direction B. Therefore, the first plane 21, the third plane 23a, the third plane 23b, the third plane 23c, and the second plane 22 are arranged in this order as the distance from the tip 8 increases in the circumferential direction B in the second blade surface portion 6 of this embodiment. Further, the planes adjacent to each other in the circumferential direction B are continuous via ridge portions 41, 42, 43 and 44, which will be described later, which are ridgelines at which the planes intersect with each other (see FIG. 2C).

As illustrated in FIG. 3B, the respective three third planes 23a, 23b and 23c have different distances L from the center plane X, and an angle θ3a of the third plane 23a closest to the center plane X is larger than angles θ3b and θ3c of the other two third planes 23b and 23c. The angle θ3c of the third plane 23c farthest from the center plane X is smaller than the angles θ3a and θ3b of the other two third planes 23a and 23b. That is, the angles θ of the three third planes 23a, 23b, and 23c with respect to the center plane X in the orthogonal cross-section gradually decrease as the distance L from the center plane X increases.

Therefore, the first plane 21, the second plane 22, and the plurality of third planes 23 of the second blade surface portion 6 of this embodiment have the smaller angle θ with respect to the center plane X in the orthogonal cross-section as the distance L (see FIG. 3B) from the center plane X in the orthogonal cross-section is farther. Therefore, the angle θ gradually decreases in the order of the first plane 21, the third plane 23a, the third plane 23b, the third plane 23c, and the second plane 22 in this embodiment. That is, the angle θ gradually decreases in the order of the angle θ1 of the first plane 21, the angle θ3a of the third plane 23a, the angle θ3b of the third plane 23b, the angle θ3c of the third plane 23c, and the angle θ2 of the second plane 22 as illustrated in FIGS. 3A to 3F.

Here, the angle θ1 of the first plane 21 does not change depending on the position in the central axis direction A as illustrated in FIGS. 3B to 3F. That is, the angle θ1 of the first plane 21 is constant regardless of the position in the central axis direction A.

The angle θ2 of the second plane 22 is also constant regardless of the position in the central axis direction A.

Further, the angle θ3 of the third plane 23 is also constant regardless of the position in the central axis direction A. More specifically, the angle θ3a of the third plane 23a, which is one of the plurality of third planes 23, is constant regardless of the position in the central axis direction A. Further, the angle θ3b of the third plane 23b, which is one of the plurality of third planes 23, is also constant regardless of the position in the central axis direction A. Further, the angle θ3c of the third plane 23c, which is one of the plurality of third planes 23, is also constant regardless of the position in the central axis direction A.

The third blade surface portion 7 of this embodiment has a shape symmetric with the second blade surface portion 6 with respect to the center plane X. Thus, the third blade surface portion 7 of this embodiment also includes a first plane, a second plane, and a plurality of third planes similarly to the second blade surface portion 6, and has an angular relationship similar to the angular relationship of the angle θ among the first plane 21, the second plane 22, and the plurality of third planes 23 of the second blade surface portion 6 although the description thereof is omitted. The second blade edge 9b of this embodiment also has a shape symmetric with the first blade edge 9a with respect to the center plane X.

Figure 4A:
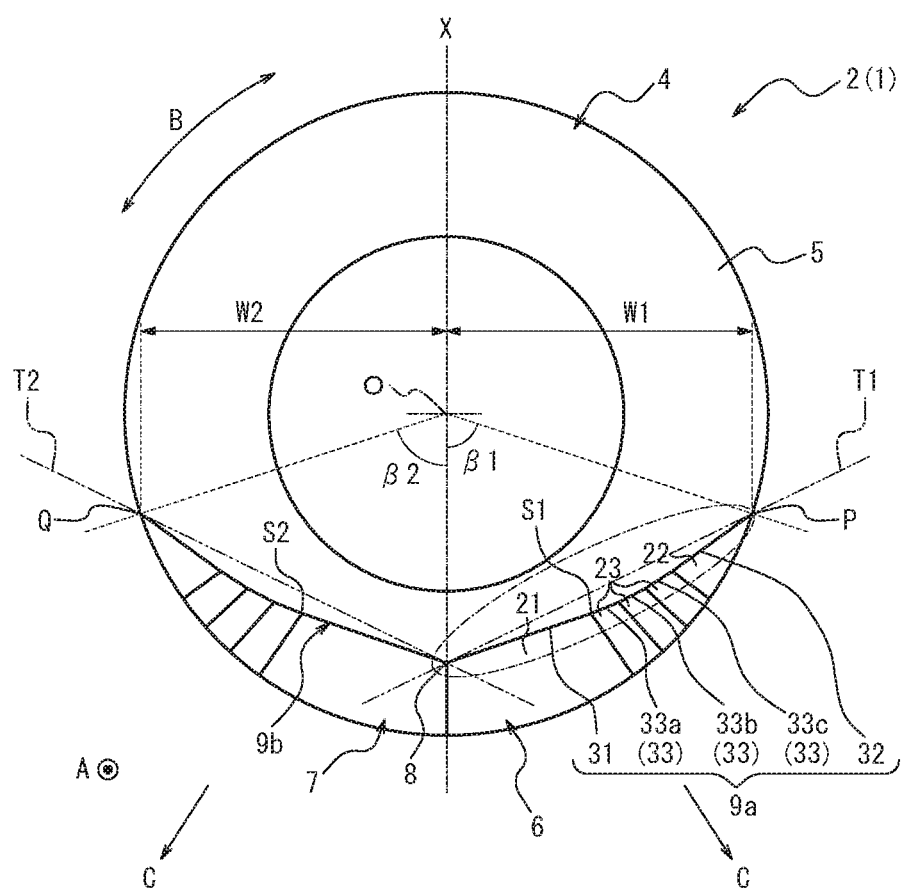
FIG. 4A is a view of a blade surface 4 of the puncture needle 1 as viewed from a tip 8 side along a central axis direction A.

FIG. 4A is a view illustrating a distal end view of the blade surface 4 as viewed from the tip 8 side along the central axis direction A. In the distal end view (see FIG. 4A), the second plane 22 is at a position farther from the tip 8 than the first plane 21. In other words, the second plane 22 is at a position farther from the center plane X than the first plane 21 in the orthogonal cross-section (see FIGS. 3A to 3F).

Further, the arbitrary one third plane 23 out of the plurality of third planes 23 is at a position farther from the tip 8 than the first plane 21 and at a position closer to the tip 8 than the second plane 22 in the distal end view as illustrated in FIG. 4A. In other words, the arbitrary one third plane 23 is at a position farther from the center plane X than the first plane 21 and at a position closer to the center plane X than the second plane 22 in the orthogonal cross-section (see FIGS. 3A to 3F).

As described above, the second plane 22 of the second blade surface portion 6 is at the position farther from the tip 8 than the first plane 21 of the second blade surface portion 6 in the distal end view (see FIG. 4A), and the angle θ2 (see FIG. 3B) of the second plane 22 with respect to the center plane X in the orthogonal cross-section is smaller than the angle θ1 (see FIG. 3B) of the first plane 21 with respect to the center plane X in the orthogonal cross-section. With such a configuration, it is possible to secure a longer length of the first blade edge 9a formed by the ridgeline between the first blade surface portion 5 and the second blade surface portion 6 as compared with the second blade surface portion configured using only one plane having the angle θ1 with respect to the center plane X in the orthogonal cross-section being equal to the angle θ1 of the first plane 21. In addition, with the above-described configuration, it is possible to secure a longer length of the first blade edge 9a even as compared with the second blade surface portion configured using only one plane having the angle θ1 with respect to the center plane X in the orthogonal cross-section being smaller than the angle θ1 of the first plane 21 and larger than the angle θ1 of the second plane 22. In addition, it is possible to enlarge an incision on the skin as compared with the second blade surface portion configured using only one plane having the angle θ1 with respect to the center plane X in the orthogonal cross-section being smaller than the angle θ1 of the first plane 21 and larger than the angle θ1 of the second plane 22.

Figure 5:
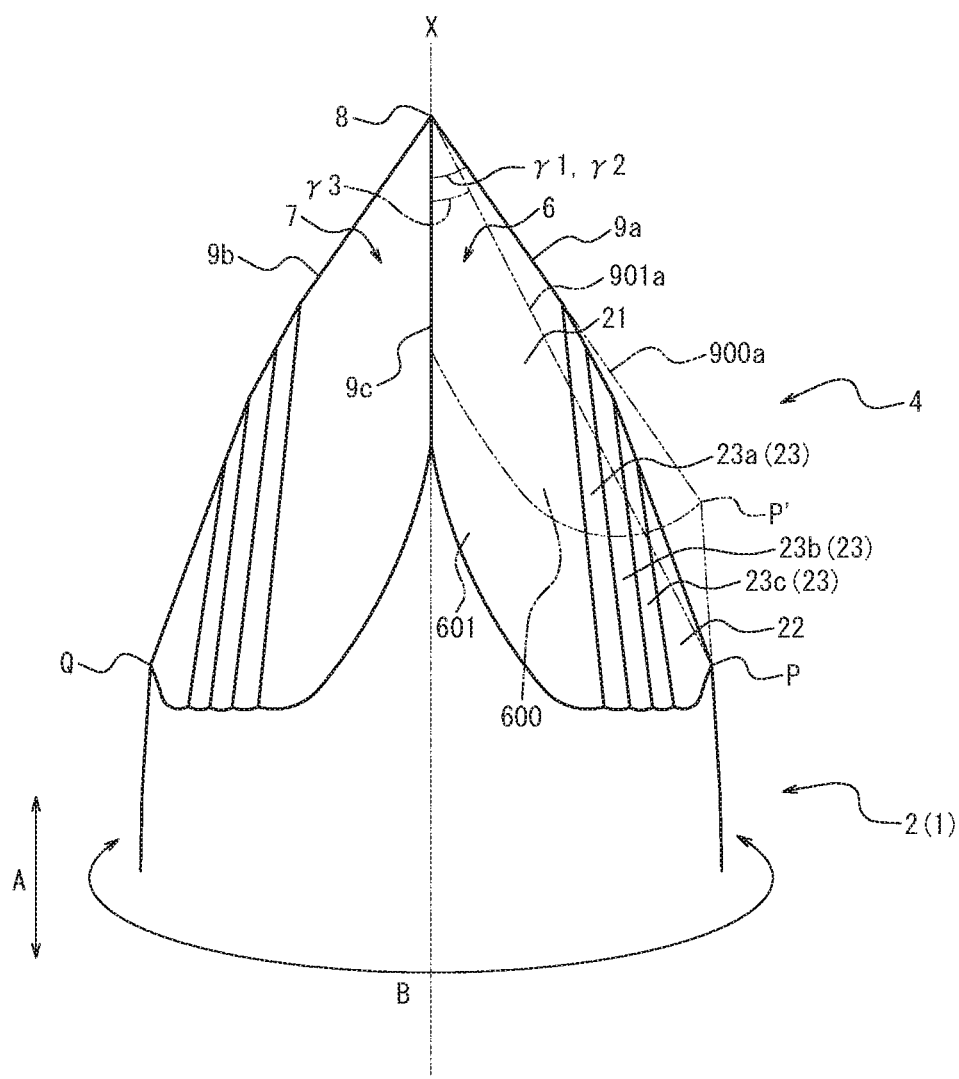
FIG. 5 is a view comparing a second blade surface portion 6 of the puncture needle 1 with a comparative example thereof.

The above-described operational effect will be described with reference to FIGS. 5 and 6. FIG. 5 is a view further enlarging the vicinity of the tip 8 in FIG. 2C. However, in FIG. 5, a second blade surface portion 600 configured using only one plane having the angle θ (see FIGS. 3A to 3F) with respect to the center plane X in the orthogonal cross-section being equal to the angle θ of the first plane 21 is indicated by a two-dot chain line as a comparative example of the second blade surface portion 6 of this embodiment. As illustrated in FIG. 5, the first blade edge 9a formed by an intersection between the second blade surface portion 6 and the first blade surface portion 5 (see FIGS. 1A to 1D and the like) has a tip angle γ1 in the rear view. Further, a comparative blade edge 900a formed by an intersection between the second blade surface portion 600 as the comparative example and the first blade surface portion 5 (see FIGS. 1A to 1D and the like) has a tip angle γ2 in the rear view as illustrated in FIG. 5. As illustrated in FIG. 5, the tip angle γ1 of the first blade edge 9a in the rear view is equal to the tip angle γ2 of the comparative blade edge 900a in the rear view. The "tip angle of the blade edge in the rear view" herein refers to an angle between an imaginary line that passes through the tip and extends parallel to the central axis direction A, and the blade edge, in the rear view (see FIG. 5).

However, the first blade edge 9a can be made longer than the comparative blade edge 900a according to the second blade surface portion 6 as illustrated in FIG. 5. Specifically, because the second blade surface portion 6 has the second plane 22 in addition to the first plane 21, a position of the terminal point P of the first blade edge 9a can be formed to be closer to the proximal end side in the central axis direction A than a terminal point P' of the comparative blade edge 900a. As a result, the length of the first blade edge 9a can be secured to be longer than that of the comparative blade edge 900a. As a result, it is possible to enlarge a cut width W1 (see FIG. 4A) to be described later. Details of the cut width W1 will be described later.

Further, in FIG. 5, a second blade surface portion 601 configured using only one plane having the angle θ (see FIGS. 3A to 3F) with respect to the center plane X in the orthogonal cross-section being smaller than the angle θ of the first plane 21 and larger than the angle θ of the second plane 22 is indicated by a two-dot chain line as another comparative example of the second blade surface portion 6 of this embodiment. As illustrated in FIG. 5, formation regions in the central axis direction A of the second blade surface portion 6 and the second blade surface portion 601 as the comparative example are the same. However, the tip angle γ1 of the first blade edge 9a in the rear view (see FIG. 5) is larger than a tip angle γ3 of a comparative blade edge 901a in the rear view (see FIG. 5) when comparing the first blade edge 9a formed by the intersection between the second blade surface portion 6 and the first blade surface portion 5 (see FIGS. 1A to 1D and the like) and the comparative blade edge 901a formed by an intersection between the second blade surface portion 601 and the first blade surface portion 5 (see FIGS. 1A to 1D and the like) as the comparative example. In other words, the second blade surface portion 6 is formed such that the first blade edge 9a protrudes outward to be convex in the rear view (see FIG. 5) as compared to the comparative blade edge 901a. Thus, the length of the first blade edge 9a can be secured to be longer than that of the comparative blade edge 901a.

Figure 6:
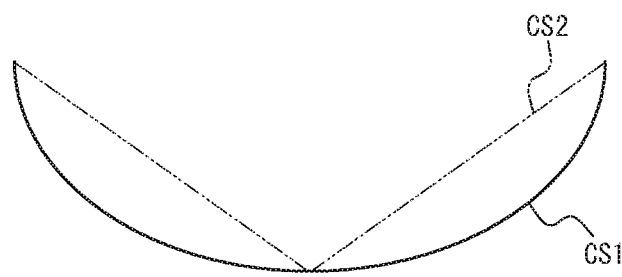
FIG. 6 is a view comparing an incision formed by the second blade surface portion 6 of the puncture needle 1 with an incision formed by a second blade surface portion as the comparative example.

FIG. 6 is a view comparing an incision CS1 on the skin formed by the first blade edge 9a illustrated in FIG. 5 with an incision CS2 on the skin formed by the comparative blade edge 901a illustrated in FIG. 5. More specifically, FIG. 6 illustrates the incision CS1 formed when the first blade edge 9a (see FIG. 5) is formed to be symmetric with respect to the center plane X (see FIG. 5). In addition, FIG. 6 illustrates the incision CS2 formed when the comparative blade edge 901a (see FIG. 5) is formed to be symmetric with respect to the center plane X. As described above, because the first blade edge 9a is longer than the comparative blade edge 901a, a length of the incision CS1 formed by the first blade edge 9a at the time of puncture can be made longer than a length of the incision CS2 formed by the comparative blade edge 901a as illustrated in FIG. 6. That is, the incision CS1 formed by the first blade edge 9a at the time of puncture can be made larger than the incision CS2 formed by the comparative blade edge 901a. As a result, the incision is close to a sectional shape of the body portion 2, and thus, it is possible to reduce the penetration resistance during passage of a jaw portion 15 (see FIG. 2A), which is a proximal end in the central axis direction A of the inner edge 13 (see FIG. 2A and the like) of the first blade surface portion 5 (see FIGS. 1A to 1D and the like) and an outer circumferential surface of the body portion 2 at the time of puncturing. In addition, when the puncture needle 1 is used, for example, as an inner needle of an indwelling needle, it is also possible to reduce the penetration resistance caused by a step between the puncture needle 1 and a catheter as an outer needle of the indwelling needle.

Further, the first blade edge 9a can be made more smoothly continuous with the outer circumferential surface of the body portion 2 on the proximal end side in the central axis direction A as compared with the comparative blade edges 900a and 901a. That is, the first blade edge 9a and the proximal-end-side outer edge portion 17 can be made smoothly continuous such that no corner portion is formed at the terminal point P as illustrated in FIG. 2A.

As described above, the second blade surface portion 6 and the third blade surface portion 7 have the shape symmetric with respect to the center plane X. Therefore, the third blade surface portion 7 also has the above operational effect similarly to the second blade surface portion 6. However, only the second blade surface portion 6 may be configured to include at least the first plane 21 and the second plane 22, and the third blade surface portion 7 may be configured so as not to include a plurality of planes. However, if both the second blade surface portion 6 and the third blade surface portion 7 are configured to include the first plane 21 and the second plane 22 as in this embodiment, it is possible to secure a longer total length of the first blade edge 9a and the second blade edge 9b, that is, a longer length from the terminal point P to the terminal point Q via the tip 8 on the outer edge 14 of the first blade surface portion 5 as compared with the case where only the second blade surface portion 6 is configured to include the first plane 21 and the second plane 22. Details of the lengths of the first blade edge 9a and the second blade edge 9b will be described later (see FIGS. 4A and 4B).

As a material of the puncture needle 1 in this embodiment, a metal material such as stainless steel, aluminum or an aluminum alloy, and titanium or a titanium alloy can be used.

Hereinafter, each configuration and characteristic portions of the body portion 2 of this embodiment will be described in detail.

The body portion 2 of this embodiment is a pipe body having a uniform inner diameter of an inner circumferential surface and a uniform outer diameter of the outer circumferential surface in the central axis direction A. The body portion 2 has a proximal end portion, which is an end portion on the opposite side to the distal end portion 3 in the central axis direction A, connected to a medical instrument such as a syringe and a connector of a transfusion line via a needle hub or the like.

In this embodiment, the inner circumferential surface of the tubular body portion 2 includes the hollow portion 10, and the inner diameter of the inner circumferential surface and the outer diameter of the outer circumferential surface are uniform in the central axis direction A. However, the invention is not limited to this configuration. For example, the inner diameter of the inner circumferential surface and the outer diameter of the outer circumferential surface of the body portion 2 may gradually decrease from the proximal end side toward the tip 8 in the central axis direction A. Further, for example, it is also possible to configure the outer diameter of the body portion 2 in a tapered shape to decrease from the proximal end side toward the tip 8 in the central axis direction A, and the inner diameter of the body portion 2 to be uniform in the central axis direction A. Further, it is possible to adopt various configurations regarding the inner diameter and the outer diameter of the body portion 2 in accordance with the use of the puncture needle 1, such as a configuration in which a portion where the inner diameter gradually decreases or increases in the central axis direction A toward the tip 8 is provided in a partial region in the central axis direction A.

As illustrated in FIGS. 1B and 2B, the first blade surface portion 5 is a plane inclined with respect to the central axis direction A, and one end of the first blade surface portion 5 is the tip 8, and the other end thereof is continuous with the outer circumferential surface of the body portion 2 in the central axis direction A. An inclination angle of the first blade surface portion 5 with respect to the central axis direction A is larger than an inclination angle of the outer circumferential surface of the body portion 2 with respect to the central axis direction A in a cross section parallel to the central axis direction A. In this embodiment, the outer diameter of the body portion 2 of the puncture needle 1 is uniform in the central axis direction A, and the outer circumferential surface of the body portion 2 extends in the central axis direction A in a cross-sectional view parallel to the central axis direction A. Therefore, if the first blade surface portion 5 is inclined with respect to the central axis direction A, the inclination angle of the first blade surface portion 5 is larger than the inclination angle of the outer circumferential surface of the body portion 2. However, when the body portion 2 of the puncture needle 1 is configured to have the outer diameter gradually decreasing or gradually increasing toward the tip 8 in the central axis direction A, the first blade surface portion 5 is inclined with respect to not only the central axis direction A but also the outer circumferential surface of the body portion 2 in a cross section orthogonal to the first blade surface portion 5.

Here, the outer edge 14 of the first blade surface portion 5 is constituted by the first blade edge 9a, the second blade edge 9b, and the proximal-end-side outer edge portion 17 having a convex curved shape connecting the terminal point P of the first blade edge 9a and the terminal point Q of the second blade edge 9b as illustrated in FIG. 2A.

Each of the first blade edge 9a and the second blade edge 9b is formed by a plurality of continuous straight lines. The first blade edge 9a and the proximal-end-side outer edge portion 17 are smoothly continuous such that a corner vertex becomes small at the position of the terminal point P. Further, the second blade edge 9b and the proximal-end-side outer edge portion 17 are smoothly continuous such that a corner vertex becomes small at the position of the terminal point Q. If the vertices formed at the positions of the terminal point P and the terminal point Q are small in this manner, it is possible to suppress an increase of the penetration resistance when the positions of the terminal point P and the terminal point Q pass through the skin.

As described above, the third blade edge 9c is formed by the ridgeline where the second blade surface portion 6 and the third blade surface portion 7 intersect with each other. As described above, the third blade edge 9c serves as a cutting edge that incises the skin when puncturing the human body with the puncture needle 1, and thus, it is possible to reduce the penetration resistance in the vicinity of the tip 8 at the time of puncture.

Next, the details of the first blade edge 9a and the second blade edge 9b will be described.

As described above, the second plane 22 of the second blade surface portion 6 is at the position farther from the tip 8 than the first plane 21 of the second blade surface portion 6 in the distal end view (see FIG. 4A), and the angle θ2 (see FIG. 3B) of the second plane 22 with respect to the center plane X in the orthogonal cross-section is smaller than the angle θ1 (see FIG. 3B) of the first plane 21 with respect to the center plane X in the orthogonal cross-section. With such a configuration, it is easier to secure the length of the first blade edge 9a to be much longer as compared with the case where the second blade surface portion is configured using only one plane. In other words, if the second blade surface portion 6 is configured to include the plurality of planes in this manner, it is possible to enlarge a circumferential extension range of the first blade edge 9a represented by a center angle β1 from the tip 8 to the terminal point P about the central axis O in the distal end view of the blade surface 4 as viewed from the tip 8 side as illustrated in FIG. 4A. For example, the center angle β1 of the first blade edge 9a as the circumferential extension range can be set to 50° or larger, and can be also set to 70° or larger.

Because it is possible to secure the first blade edge 9a to be longer by configuring the second blade surface portion 6 to include the plurality of planes in this manner, it is possible to enlarge the cut width W1 (see FIG. 4A) capable of incising the skin with the first blade edge 9a at the time of puncture with the puncture needle 1. That is, the second blade surface portion 6 including the first plane 21 and the second plane 22 described above can increase the cut width W1 by the first blade edge 9a as compared with the second blade surface portion configured using only one plane. Therefore, after the first blade edge 9a has passed through the skin, it is possible to suppress the pushed-apart amount of the incision of the skin that is forcibly pushed apart by the outer circumferential surface of the body portion 2 of the puncture needle 1 or an outer circumferential surface of the catheter, which is mounted around the puncture needle 1 with the puncture needle 1 as the inner needle and serves as the outer needle to be inserted together with the puncture needle 1. Therefore, it is possible to reduce the pain that the patient feels at the time of puncture. Further, if the cut width W1 can be increased, the catheter serving as the outer needle that covers the puncture needle 1 easily enters the skin and a blood vessel and it is possible to suppress rollover of the catheter at the time of puncture when the puncture needle 1 is used, for example, as the inner needle of the indwelling needle.

The third blade surface portion 7 also has the same configuration as the above-described second blade surface portion 6. Therefore, if the third blade surface portion 7 is configured to include the plurality of planes similarly to the second blade surface portion 6, it is possible to enlarge a circumferential extension range of the second blade edge 9b represented by a center angle β2 from the tip 8 to the terminal point Q about the central axis O in the distal end view of the blade surface 4 as viewed from the tip 8 side as illustrated in FIG. 4A. For example, the center angle β2 of the second blade edge 9b as the circumferential extension range can be set to 50° or larger, and can be also set to 70° or larger.

Because it is possible to secure the second blade edge 9b to be longer by configuring the third blade surface portion 7 to include the plurality of planes in this manner, it is possible to enlarge a cut width W2 (see FIG. 4A) capable of incising the skin with the second blade edge 9b at the time of puncture with the puncture needle 1. That is, the third blade surface portion 7 configured by the above-described curved surface can increase the cut width W2 by the second blade edge 9b as compared with a third blade surface configured using only one plane. Therefore, after the second blade edge 9b has passed through the skin, it is possible to suppress the pushed-apart amount of the incision of the skin that is forcibly pushed apart by the outer circumferential surface of the body portion 2 of the puncture needle 1 or the outer surface of the outer needle, which is mounted around the puncture needle 1 with the puncture needle 1 as the inner needle and inserted together with the puncture needle 1. Therefore, it is possible to reduce the pain that the patient feels at the time of puncture. Further, if the cut width W2 can be increased, the catheter serving as the outer needle that covers the puncture needle 1 easily enters the skin and a blood vessel and it is possible to suppress rollover of the catheter at the time of puncture when the puncture needle 1 is used, for example, as the inner needle of the indwelling needle.

If both the second blade surface portion 6 and the third blade surface portion 7 are configured to include the plurality of planes as in this embodiment, it is possible to further increase the sum of the cut width W1 by the first blade edge 9a and the cut width W2 by the second blade edge 9b as compared with that of the case where only the second blade surface portion 6 includes the plurality of planes, which is preferable.

Further, the first blade edge 9a of this embodiment includes a first blade edge portion 31, a second blade edge portion 32, and a plurality of third blade edge portions 33 as illustrated in FIG. 4A.

The first blade edge portion 31 is formed by a ridgeline where the first blade surface portion 5 and the first plane 21 of the second blade surface portion 6 intersect with each other. The first blade edge portion 31 of this embodiment extends to the tip 8. Further, the second blade edge portion 32 is formed by a ridgeline where the first blade surface portion 5 and the second plane 22 of the second blade surface portion 6 intersect with each other. The second blade edge portion 32 of this embodiment is continuous with the outer circumferential surface of the body portion 2 in the distal end view (see FIG. 4A). In other words, the first blade edge portion 31 of this embodiment forms one end portion that is continuous with the tip 8 in the first blade edge 9a extending from the tip 8 to the outer circumferential surface of the body portion 2 in the distal end view (see FIG. 4A). In addition, the second blade edge portion 32 of this embodiment forms the other end portion continuous with the outer circumferential surface of the body portion 2 in the first blade edge 9a extending from the tip 8 to the outer circumferential surface of the body portion 2 in the distal end view (see FIG. 4A). In other words, the first plane 21 of this embodiment is formed at a position closest to the tip 8 in the circumferential direction B of the body portion 2 on the second blade surface portion 6 as illustrated in FIG. 4A. Further, the second plane 22 of this embodiment is formed at a position farthest from the tip 8 in the circumferential direction B of the body portion 2 on the second blade surface portion 6.

Further, a length of the first blade edge portion 31 of this embodiment is longer than a length of the second blade edge portion 32 in the distal end view (see FIG. 4A). Because the length of the first blade edge portion 31 extending to the tip 8 is longer than the length of the second blade edge portion 32 in this manner, it is possible to provide the configuration in which it is easy to increase the tip angle γ1 of the first blade edge 9a in the rear view (see FIG. 5 and the like).

As described above, the second blade surface portion 6 of this embodiment further includes the three third planes 23 in addition to the first plane 21 and the second plane 22. The three third planes 23 of this embodiment have the different angle θ (see FIG. 3B and the like) from the first plane 21 and the second plane 22 with respect to the center plane X in the orthogonal cross-section, and are positioned between the first plane 21 and the second plane 22 in the distal end view (see FIG. 4A). Although the second blade surface portion 6 of this embodiment includes the three third planes 23, the number of the third planes 23 is not limited to be plural but may be one.

The length of the first blade edge portion 31 of this embodiment is not only longer than the length of the second blade edge portion 32 but also longer than a length of the arbitrary one third plane 23 in the distal end view (see FIG. 4A). Further, the length of the first blade edge portion 31 of this embodiment is longer than a total length obtained by adding the lengths of the plurality of (three in this embodiment) third planes 23 in the distal end view (see FIG. 4A). In this manner, it is easy to further increase the tip angle γ1 of the first blade edge 9a in the rear view (see FIG. 5 and the like). Thus, it is possible to form a larger cut width at a narrow position in the vicinity of the tip 8, and to further reduce the pain that the patient feels at the time of puncture.

In particular, the length of the first blade edge portion 31 is preferably a fourth of the total length of the first blade edge 9a or longer, and particularly preferably a third of the total length or longer.

In the distal end view (see FIG. 4A), the third blade edge portion 33 is formed at a position between the first blade edge portion 31 and the second blade edge portion 32 by a ridgeline where the first blade surface portion 5 and the third plane 23 of the second blade surface portion 6 intersect with each other. Specifically, the first blade edge 9a of this embodiment includes three third blade edge portions 33. One of the three third blade edge portions 33 is a tip-side blade edge portion 33*a* formed by a ridgeline where the first blade surface portion 5 and the third plane 23*a* closest to the tip 8 in the circumferential direction B among the three third planes 23 of the second blade surface portion 6 intersect with each other. In addition, another one of the three third blade edge portions 33 is an outer-circumference-side blade edge portion 33*c* formed by a ridgeline where the first blade surface portion 5 and the third plane 23*c* farthest from the tip 8 in the circumferential direction B among the three third planes 23 of the second blade surface portion 6 intersect with each other. In addition, the remaining one of the three third blade edge portions 33 is an intermediate blade edge portion 33*b* formed by a ridgeline where the first blade surface portion 5 and the third plane 23*b* positioned between the two third planes 23*a* and 23*c* in the circumferential direction B among the three third planes 23 of the second blade surface portion 6 intersect with each other.

Figure 4B:
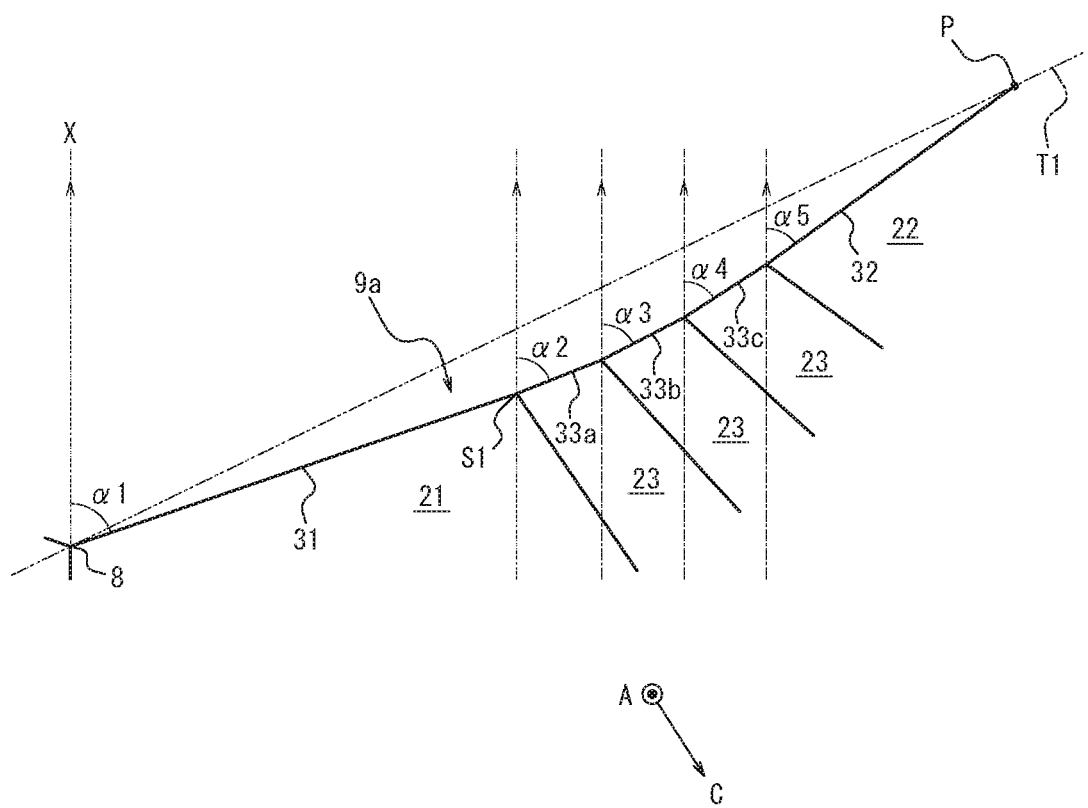
FIG. 4B is a view illustrating a portion surrounded by a one-dot chain line in FIG. 4A in an enlarged manner.

FIG. 4B is an enlarged view of a portion surrounded by the one-dot chain line in FIG. 4A. As illustrated in FIG. 4B, each blade edge portion of the first blade edge portion 31, the second blade edge portion 32, and the plurality of third blade edge portions 33 has a smaller angle α with respect to the center plane X at a position farther from the tip 8 in the distal end view (see FIG. 4A) in this embodiment. More specifically, the relationship of α1>α3*a*>α3*b*>α3*c*>α2 is satisfied as illustrated in FIG. 4B. "α1" is the angle of the first blade edge portion 31. "α3*a*" is the angle of the tip-side blade edge portion 33*a* of the third blade edge portion 33. "α3*b*" is an angle of the intermediate blade edge portion 33*b* of the third blade edge portion 33. "α3*c*" is the angle of the outer-circumference-side blade edge portion 33*c* of the third blade edge portion 33. "α2" is the angle of the second blade edge portion 32. That is, the angle α with respect to the center plane X of each of the blade edge portions constituting the first blade edge 9*a* gradually decreases as being farther from the tip 8 in the distal end view (see FIGS. 4A and 4B). With such a configuration, the length of the first blade edge 9*a* can be made longer than the length of the comparative blade edge 900*a* (see FIG. 5). Further, the shape of the blade edge 9*a* becomes smooth so that it is possible to reduce the penetration resistance.

As illustrated in FIG. 2C, the ridge portion 41 formed by the ridgeline where the second plane 22 and the third plane 23 intersect with each other, more specifically, the ridge portion 41 formed by the ridgeline where the second plane 22 and the third plane 23*c* intersect with each other extends along the central axis O. Because the extension direction of the ridge portion 41 is set to the direction along the central axis O in this manner, it is possible to prevent the ridge portion 41 from becoming a junction and increasing the penetration resistance as compared with a configuration in which a ridge portion extends to be orthogonal to the central axis O. The expression, "along the central axis O" is not limited to being parallel to the central axis O but also includes being inclined at a predetermined angle or smaller (for example, 30 degrees or smaller) with respect to the central axis O. The ridge portion 41 of this embodiment extends along the central axis O in the state of being inclined at an angle of 5 to 15 degrees with respect to the central axis O.

As illustrated in FIG. 2C, the ridge portion 42 formed by the ridgeline where the first plane 21 and the third plane 23 intersect with each other, more specifically, the ridge portion 42 formed by the ridgeline where the first plane 21 and the third plane 23*a* intersect with each other extends along the central axis O. Because the extension direction of the ridge portion 42 is set to the direction along the central axis O in this manner, it is possible to prevent the ridge portion 42 from becoming a junction and increasing the penetration resistance as compared with a configuration in which a ridge portion extends to be orthogonal to the central axis O. The ridge portion 42 of this embodiment extends along the central axis O in the state of being inclined at an angle of 5 to 15 degrees with respect to the central axis O.

Further, the other ridge portions 43 and 44 formed by the ridgelines where the plurality of third planes 23 intersect with each other also extend along the central axis O. In this manner, it is possible to prevent the ridge portions 43 and 44 from becoming a junction and increasing the penetration resistance. The ridge portions 43 and 44 of this embodiment extend along the central axis O in the state of being inclined at an angle of 5 to 15 degrees with respect to the central axis O.

In particular, the ridge portions 41, 42, 43 and 44 of this embodiment are inclined at the angle of 5 to 15 degrees so as to approach the central axis O from the proximal end side toward the tip 8 in the central axis direction A in the rear view as illustrated in FIG. 2C. Because the ridge portions 41, 42, 43 and 44 extend along the central axis O so as to approach the central axis O from the proximal end side toward the tip 8 in the central axis direction A in this manner, it is possible to further suppress the ridge portions 41, 42, 43 and 44 from causing the penetration resistance at the time of puncture.

As illustrated in FIG. 2C, the ridge portions 41, 42, 43 and 44 have a shorter length in the extension direction at a position farther from the tip 8 in the circumferential direction B.

Regarding the plurality of ridge portions arranged as described above, the ridge portion at a position farther from the central axis O in the rear view (see FIG. 2C) has a larger angle with respect to the central axis direction A than the ridge portion closer to the central axis O. Specifically, an angle of the ridge portion 41 with respect to the central axis direction A is larger than an angle of the ridge portion 42 with respect to the central axis direction A in the rear view (see FIG. 2C).

As described above, the third blade surface portion 7 of this embodiment has a shape symmetric with the second blade surface portion 6 with respect to the center plane X, and has the same operational effect as that of the second blade surface portion 6, and thus, the description thereof will be omitted here.

In this embodiment, the area of the first plane 21 is larger than the area of the second plane 22 in the second blade surface portion 6 as illustrated in FIG. 5. The total area of the first plane 21, the second plane 22, and the third plane 23 in the second blade surface portion 6 is larger than the area of the second blade surface portion 601 (see FIG. 5) configured using only one plane as the comparative example. In this manner, it is possible to maintain favorable rectilinearity of the puncture needle 1 at the time of being inserted from the skin to pass through a living tissue.

In the distal end view (see FIG. 4A), the first blade edge 9*a* extends to protrude to the radially outer side of the body portion 2 (a direction indicated by an arrow "C" in FIG. 4A) from a straight line T1 connecting both ends of the first blade edge 9*a*. The straight line T1 connecting both the ends of the first blade edge 9*a* in the distal end view illustrated in FIG. 4A means a virtual straight line passing through the tip 8 and the terminal point P of the first blade edge 9*a*. With such a configuration, it is possible to secure the longer length of the first blade edge 9*a*.

In the distal end view (see FIG. 4A), the second blade edge 9b extends to protrude to the radially outer side of the body portion 2 (the direction indicated by the arrow "C" in FIG. 4A) from a straight line T2 connecting both ends of the second blade edge 9b. The straight line T2 connecting both the ends of the second blade edge 9b in the distal end view illustrated in FIG. 4A means a virtual straight line passing through the tip 8 and the terminal point Q of the second blade edge 9b. With such a configuration, it is possible to secure the longer length of the second blade edge 9b.

As described above, the first blade edge 9a includes the first blade edge portion 31, which extends to the tip 8 and is formed by the ridgeline where the first blade surface portion 5 (see FIGS. 1A to 1D and the like) and the first plane 21, which is one of the plurality of planes (the first plane 21, the second plane 22, and the three third planes 23 in this embodiment) having the different angles with respect to the center plane X in the orthogonal cross-section (see FIGS. 3A to 3F) intersect with each other. As illustrated in FIG. 4B, the first blade edge portion 31 extends from the tip 8 to a terminal point S1, which is positioned on the radially outer side of the body portion 2 (the direction indicated by the arrow "C" in FIG. 4B) than the straight line T1 connecting both the ends of the first blade edge 9a, in the distal end view of the blade surface 4 (see FIGS. 1A to 1D and the like) as viewed from the tip 8 side along the central axis direction A. In this manner, it is possible to secure the longer length of the first blade edge 9a. The second blade edge 9b also has the same configuration. That is, the first blade edge portion 31 of the second blade edge 9b also extends from the tip 8 to a terminal point S2, which is positioned on the radially outer side of the body portion 2 than the straight line T2 connecting both the ends of the second blade edge 9b, in the distal end view of the blade surface 4 (see FIGS. 1A to 1D and the like) as viewed from the tip 8 side along the central axis direction A.

The puncture needle according to the present disclosure can be realized by various specific configurations, and is not limited to the above-described configuration. Various modifications and changes can be made without departing from the gist of the invention described in the claims. For example, the body portion 2 of the puncture needle 1 illustrated in FIGS. 1A to 1D has a substantially circular cross-sectional outline of an arbitrary transverse cross-section, but the invention is not limited to this configuration. For example, the body portion 2 may be configured as a body portion whose arbitrary transverse cross-section has a substantially elliptical cross-sectional outline, or a body portion whose arbitrary transverse cross-section has any cross-sectional outline of a substantially circular shape and a substantially elliptical shape. Further, the body portion 2 may be a body portion having a part where a cross-sectional outline becomes a substantially circular shape or a substantially elliptical shape. Further, any shape having an oval cross-sectional outline defined by the major axis and the minor axis may be used as a shape other than the circular shape, and may be, for example, a rounded rectangle obtained by combining a semicircle to both short sides of a rectangular without being limited the above-described elliptical shape.

Figure 7:
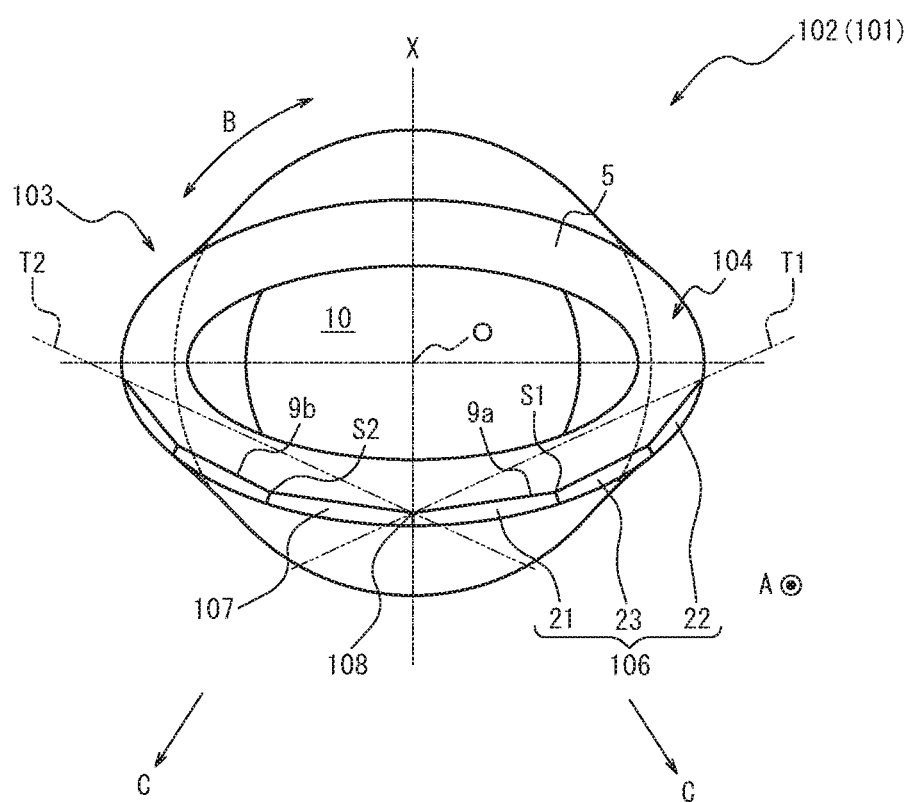
FIG. 7 is a view of a blade surface 104 of a puncture needle 101 as a modification of the puncture needle 1 as viewed from a tip 108 side along the central axis direction A.

FIG. 7 is a view illustrating a distal end view of a blade surface 104 of a puncture needle 101 as viewed from a tip 108 side. As illustrated in FIG. 7, a body portion 102, provided with a distal end portion 103 having an elliptical outer circumferential surface in a distal end view, may be configured. In the body portion 102 illustrated in FIG. 7, the shape of the outer circumferential surface at a position of the distal end portion 103 is different from that of the above-described body portion 2 (see FIGS. 1A to 1D and the like). Further, the number of planes in a second blade surface portion 106 and a third blade surface portion 107 of the body portion 102 illustrated in FIG. 7 is different from that of the above-described body portion 2 (see FIGS. 1A to 1D and the like). The other configurations of the body portion 102 illustrated in FIG. 7 are the same as those of the above-described body portion 2. That is, the blade surface 104 is formed at the distal end portion 103 of the body portion 102 illustrated in FIG. 7, and the blade surface 104 includes the first blade surface portion 5, the second blade surface portion 106, and the third blade surface portion 107. The second blade surface portion 106 illustrated in FIG. 7 is constituted by the first plane 21, the second plane 22, and the single third plane 23. The third blade surface portion 107 illustrated in FIG. 7 has a shape symmetric with the second blade surface portion 106 with respect to the center plane X.

In this manner, a shape of the outer circumferential surface of the body portion and the number of planes of the second blade surface portion and the third blade surface portion are not particularly limited and can be appropriately designed.

What is claimed is:

1. A medical puncture needle comprising:
   a rod-shaped body portion; and
   a blade surface formed at a distal end portion of the rod-shaped body portion;
   wherein:
   the blade surface comprises:
      a first blade surface portion that is inclined with respect to a central axis of the body portion and extends to a tip, wherein the first blade surface portion extends from a proximal end of the blade surface to a distal end of the blade surface in a single plane, and
      a second blade surface portion that is formed on a back side of the first blade surface portion, the second blade surface portion comprising:
         a first planar surface that extends in a first plane, and
         a second planar surface that extends in a second plane,
         wherein the first plane and the second plane have different angles with respect to a virtual plane that includes the central axis and passes through the tip at an orthogonal cross-section that is orthogonal to the central axis,
         wherein the second planar surface is at a position farther from the tip than the first planar surface in a distal end view of the blade surface as viewed from a tip side along a central axis direction, and
         wherein the angle of the second plane with respect to the virtual plane in the orthogonal cross-section is smaller than the angle of the first plane with respect to the virtual plane in the orthogonal cross-section,
      wherein a blade edge extending to the tip is formed by a ridgeline at which the first blade surface portion intersects the second blade surface portion, wherein the blade edge comprises:
         a first blade edge portion formed by a first ridgeline portion at which the first blade surface portion intersects the first planar surface of the second blade surface portion, and
         a second blade edge portion formed by a second ridgeline portion at which the first blade surface portion intersects the second planar surface of the second blade surface portion, wherein the second blade edge portion is continuous with an outer circumferential surface of the body portion in the distal end view,
wherein a length of the first blade edge portion is longer than a length of the second blade edge portion in the distal end view.

2. The medical puncture needle according to claim 1, wherein:
the second blade surface portion comprises at least one third planar surface that extends in at least one third plane, wherein the at least one third planar surface is positioned between the first planar surface and the second planar surface in the distal end view, the at least one third plane having a different angle than the first plane and the second plane with respect to the virtual plane in the orthogonal cross-section; and
the angle of the at least one third plane with respect to the virtual plane in the orthogonal cross-section is smaller than the angle of the first plane with respect to the virtual plane in the orthogonal cross-section, and is larger than the angle of the second plane with respect to the virtual plane in the orthogonal cross-section.

3. The medical puncture needle according to claim 2, wherein:
the blade edge comprises at least one third blade edge portion formed by a third ridgeline portion at which the first blade surface portion intersects the at least one third planar surface of the second blade surface portion, the at least one third blade edge portion being at a position between the first blade edge portion and the second blade edge portion in the distal end view; and
each of the first blade edge portion, the second blade edge portion, and the at least one third blade edge portion has a smaller angle with respect to the virtual plane at a position farther from the tip in the distal end view.

4. The medical puncture needle according to claim 3, wherein:
a length of the first blade edge portion is longer than a total length of the at least one third blade edge portion, in the distal end view.

5. The medical puncture needle according to claim 2, wherein:
a ridge portion is formed by a ridgeline portion at which the second planar surface intersects the at least one third planar surface.

6. The medical puncture needle according to claim 2, wherein:
a ridge portion is formed by a ridgeline portion at which the first planar surface intersects the at least one third planar surface.

7. The medical puncture needle according to claim 1, wherein:
the blade edge is a first blade edge;
the blade surface comprises a third blade surface portion that is formed on the back side of the first blade surface portion;
a second blade edge extending to the tip is formed by a second ridgeline at which the first blade surface portion intersects the third blade surface portion; and
a third blade edge extending to the tip is formed along the central axis by a third ridgeline at which the second blade surface portion intersects the third blade surface portion.

8. The medical puncture needle according to claim 7, wherein:
the third blade surface portion and the second blade surface portion are symmetric with respect to the virtual plane.

9. A medical puncture needle comprising:
a rod-shaped body portion; and
a blade surface formed at a distal end portion of the rod-shaped body portion;
wherein:
the blade surface comprises:
a first blade surface portion that is inclined with respect to a central axis of the body portion and extends to a tip, wherein the first blade surface portion extends from a proximal end of the blade surface to a distal end of the blade surface in a single plane, and
a second blade surface portion that is formed on a back side of the first blade surface portion, wherein the second blade surface portion comprises:
a first planar surface that extends in a first plane,
a second planar surface that extends in a second plane, and
at least one third planar surface that extends in at least one third plane, wherein the at least one third planar surface is positioned between the first planar surface and the second planar surface in a distal end view of the blade surface as viewed from a tip side along a central axis direction,
wherein the first plane, the second plane, and the at least one third plane have different angles with respect to a virtual plane passing through the tip and including the central axis in an orthogonal cross-section that is orthogonal to the central axis, and
wherein the second planar surface is at a position farther from the tip than the first planar surface in the distal end view,
wherein a blade edge extending to the tip is formed by a ridgeline at which the first blade surface portion intersects the second blade surface portion, wherein the blade edge comprises:
a first blade edge portion that extends to the tip and is formed by a first ridgeline portion at which the first blade surface portion intersects the first planar surface of the second blade surface portion,
a second blade edge portion that is continuous to an outer circumferential surface of the body portion in the distal end view and is formed by a second ridgeline portion at which the first blade surface portion intersects the second planar surface of the second blade surface portion, and
at least one third blade edge portion that is formed by a third ridgeline portion at which the first blade surface portion intersects the third planar surface of the second blade surface portion, the at least one third blade edge portion at least one being located at a position between the first blade edge portion and the second blade edge portion in the distal end view,
wherein a length of the first blade edge portion is longer than a total length of the at least one third blade edge portion, in the distal end view.

10. A medical puncture needle comprising:
a rod-shaped body portion; and
a blade surface formed at a distal end portion of the rod-shaped body portion;
wherein:
the blade surface comprises:

a first blade surface portion that is inclined with respect to a central axis of the body portion and extends to a tip, wherein the first blade surface portion extends from a proximal end of the blade surface to a distal end of the blade surface in a single plane, and a second blade surface portion that is formed on a back side of the first blade surface portion, the second blade surface portion comprising:
  a first planar surface that extends in a first plane, and
  a second planar surface that extends in a second plane, and
  at least one third planar surface that extends in at least one third plane, wherein the at least one third planar surface is positioned between the first planar surface and the second planar surface in a distal end view of the blade surface as viewed from a tip side along a central axis direction,
  wherein the first plane, the second plane, and the at least one third plane have different angles with respect to a virtual plane passing through the tip and including the central axis in an orthogonal cross-section that is orthogonal to the central axis,
  wherein the second planar surface is at a position farther from the tip than the first planar surface in the distal end view,
  wherein the angle of the second plane with respect to the virtual plane in the orthogonal cross-section is smaller than the angle of the first plane with respect to the virtual plane in the orthogonal cross-section, and
  wherein the angle of the at least one third plane with respect to the virtual plane in the orthogonal cross-section is smaller than the angle of the first plane with respect to the virtual plane in the orthogonal cross-section, and is larger than the angle of the second plane with respect to the virtual plane in the orthogonal cross-section,
wherein a blade edge extending to the tip is formed by a ridgeline at which the first blade surface portion intersects the second blade surface portion, wherein the blade edge comprises:
  a first blade edge portion formed by a first ridgeline portion at which the first blade surface portion intersects the first planar surface of the second blade surface portion, and
  a second blade edge portion formed by a second ridgeline portion at which the first blade surface portion intersects the second planar surface of the second blade surface portion, wherein the second blade edge portion is continuous with an outer circumferential surface of the body portion in the distal end view.

11. The medical puncture needle according to claim 10, wherein:
  the blade edge comprises at least one third blade edge portion formed by a third ridgeline portion at which the first blade surface portion intersects the at least one third planar surface of the second blade surface portion, the at least one third blade edge portion being at a position between the first blade edge portion and the second blade edge portion in the distal end view; and
  each of the first blade edge portion, the second blade edge portion, and the at least one third blade edge portion has a smaller angle with respect to the virtual plane at a position farther from the tip in the distal end view.

12. The medical puncture needle according to claim 11, wherein:
  a length of the first blade edge portion is longer than a total length of the at least one third blade edge portion, in the distal end view.

13. The medical puncture needle according to claim 10, wherein:
  a ridge portion is formed by a ridgeline portion at which the second planar surface intersects the at least one third planar surface.

14. The medical puncture needle according to claim 10, wherein:
  a ridge portion is formed by a ridgeline portion at which the first planar surface intersects the at least one third planar surface.

15. The medical puncture needle according to claim 10, wherein:
  the blade edge is a first blade edge;
  the blade surface comprises a third blade surface portion that is formed on the back side of the first blade surface portion;
  a second blade edge extending to the tip is formed by a second ridgeline at which the first blade surface portion intersects the third blade surface portion; and
  a third blade edge extending to the tip is formed along the central axis by a third ridgeline at which the second blade surface portion intersects the third blade surface portion.

16. The medical puncture needle according to claim 15, wherein:
  the third blade surface portion and the second blade surface portion are symmetric with respect to the virtual plane.

* * * * *